(12) United States Patent
Linse et al.

(10) Patent No.: US 6,379,975 B1
(45) Date of Patent: *Apr. 30, 2002

(54) METHODS AND REAGENTS FOR DETERMINING PROTEIN S

(75) Inventors: Sara Linse, Lund; Björn Dahlbäck, Malmö, both of (SE)

(73) Assignee: T.A.C. Thrombosis and Coagulation Aktiebolag, Malmo (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,285

(22) Filed: Nov. 25, 1997

Related U.S. Application Data

(60) Provisional application No. 60/035,363, filed on Jan. 10, 1997.

(30) Foreign Application Priority Data

Nov. 27, 1996 (SE) ................................. 9604378

(51) Int. Cl.[7] ..................... G01N 33/543; G01N 33/566
(52) U.S. Cl. ..................... 436/501; 435/7.94; 436/518; 436/821
(58) Field of Search .................. 435/7.94; 436/501, 436/518, 821

(56) References Cited

U.S. PATENT DOCUMENTS

| | | | |
|---|---|---|---|
| 5,405,946 A | 4/1995 | Griffin et al. | 530/380 |
| 5,597,700 A | * 1/1997 | Konstantinov et al. | 435/7.92 |

FOREIGN PATENT DOCUMENTS

| | | |
|---|---|---|
| EP | 0271810 | 6/1988 |
| WO | WO/9301209 | 1/1993 |

OTHER PUBLICATIONS

Dialog Information Services, file 155, Medline, Dialog Accession No. 08386034, Medline Acession No. 94331522, Amiral J. et al.
Dialog Information Services, file 155, Medline, Dialog Accession No. 08705565, Medline Accession No. 96355432, Hardig Y. et al.
Dahlback, Thromb. And Haemostasis, vol. 66 (1), pp. 49–61 (1991).
Zoller et al., Blood, vol. 85, No. 12, pp. 3518–3523 (Jun. 15, 1995).
Dahlback et al., Proc. Natl. Acad. Sci. USA, vol. 85, pp. 4199–4203 (Jun. 1986).
Dahlback et al., J. Biological Chemistry, vol. 265, No. 14, pp. 8127–8135 (May 15, 1990).
Hardig et al., J. Biological Chemistry, vol. 271, No. 271, No. 34, pp. 20861–20867 (Aug. 23, 1996).
Analytical Biochemistry, vol. 10, No. 2, pp. 358–361 (Feb. 1965).
Edson et al., Am. J. Clin. Path., vol. 94, pp. 176–186 (1990).
Amiral et al., Blood Coagulation and Fibrinolysis, vol. 5, pp. 179–186 (1994).
Wolfe et al., Blood Coagulation and Fibrinolysis, vol. 5, pp. 187–192 (1994).
Dahlback et al., The Molecular Basis of Blood Disease, pp. 599–627 (1994).
Fernandez et al., J. Biological Chemistry, vol. 269, No. 4, pp. 2535–250 (Jan. 28, 1994).
Fernandez et al., J. Biological Chemistry, vol. 268, No. 22, pp. 16788–16794 (Apr. 5, 1993).
Lundwall et al., Proc. Natl. Acad. Sci. USA, vol. 83, pp. 6716–6720 (Sep. 1986).
Comp et al., Blood, vol. 67, No. 2, pp. 504–508 (Feb. 1986).
Koehler et al., Nature, vol. 256, pp. 495–497 (Aug. 7, 1975).

* cited by examiner

*Primary Examiner*—David Saunders
(74) *Attorney, Agent, or Firm*—Testa, Hurwitz & Thibeault LLP

(57) ABSTRACT

The present invention is concerned with an assay for free protein S comprising addition of a ligand specific for free protein S to a biological fluid sample to form a protein S/ligand complex, and subsequent determination of the amount of said complex formed in the sample. The ligand specific for free protein S is comprised of the C4b binding protein (C4BP) or part thereof or a compound comprising an amino acid residue sequence that binds specifically to the binding site for C4BP in protein S. The present invention is further concerned with antibodies specific for free protein S, which can be used as ligands in the assay of the invention, and with protein S related polypeptides, which can be used to produce such antibodies. In addition, the present invention is related to diagnostic test systems, suitable in kit form, comprising the present ligand and at least one further reagent required in the assay for free protein S.

9 Claims, 3 Drawing Sheets

METHODS AND REAGENTS FOR DETERMINING PROTEIN S

This application claims benefit of copending U.S. Provisional Patent Application Ser. No. 60/035,363, filed Jan. 10, 1997.

The present invention is related to detection and determination of protein S in biological fluids and to reagents for use therein. More specifically, free protein S is determined as a receptor/ligand complex formed between free protein S and a molecule comprising a ligand that binds specifically to protein S.

Protein S is a member of the naturally occurring anticoagulant protein C system (a part of the blood coagulation system) and acts as a cofactor to the activated state of protein C, APC (Activated Protein C), the other cofactor being intact Factor V. This system expresses anticoagulant action since APC acts so as to degrade the coagulation promoting Factors $V_a$ and $VIII_a$.

In human plasma, protein S circulates both as free protein and in complex with another plasma protein, the C4b-binding protein (C4BP) (Dahlbäck, Thromb. Haemostas. 1991, 66:49–61). Approximately 60% of the total protein S in plasma is bound to C4BP and it is noteworthy that this form of protein S is not functionally active as APC-cofactor. Thus, the binding of C4BP to protein S leads to a loss of the APC-cofactor function of protein S. The importance of protein S as an anticoagulant protein is illustrated by the association between protein S deficiency and thromboembolic disorders. Homozygous deficiency, which is extremely rare, gives a neonatal fatal disease, whereas heterozygous deficiency is a risk factor for venous thrombosis in adult life. Indeed, protein C deficiency or protein S deficiency is found in approximately 5 to 10% of all individuals exhibiting venous thrombosis.

An individual having protein S deficiency, thus, runs an increased risk of experiencing venous thromboembolic events. Accordingly, methods for determining blood or plasma levels of protein S have a potential clinical use. Particularly, methods for measurement of the levels of free protein S would be appreciated, since several investigators have shown that for the diagnosis of protein S deficiency, the level of free protein S should be measured rather than the level of total protein S or the bound form of protein S (Zöller et al, Blood, 1995, 85:3524–3531). The reason for this is that higher sensitivity and specificity as regards the genetic defect causing protein S deficiency are achieved with the free protein S assays than with assays for measuring total protein S or bound protein S.

Previously known methods for determining free protein S are based on two different test principles, viz. differential polyethylene glycol precipitation properties and use of monoclonal antibodies, resp.

Methods using polyethylene glycol (PEG) to selectively remove bound protein S from a fluid comprising bound protein S and free protein S prior to measurement of protein S are based on the discovery that the complex bound form of protein S (PS:C4BP) precipitates already at a PEG concentration of approximately 3.75–5%, whereas most of the free protein S remains in solution. This principle has been used extensively in different commercially available protein S assays. Thus, in assays for free protein S, plasma samples are usually subjected to precipitation with PEG (3.75–5%) whereafter the protein S remaining in the supernatant after centrifugation is measured with immunological methods, such as ELISA, RIA or Laurell rockets. Such methods are disclosed in Am. J. Clin. Path. 94:176–186 (1990), Anal. Biochem., 10:358–361 (1985) and Blood, 67:504–508 (1986). However, these methods suffer from some disadvantages, mainly due to the PEG precipitation procedure. Thus, even when the PEG precipitation is highly standardized, this procedure is plagued by poor reproducibility and by its laborious and time consuming nature.

The second test principle mentioned above is based on use of monoclonal antibodies. Such monoclonal antibodies are specific for the free form of protein S, i.e. the epitopes for these antibodies are located at or close to the binding site for C4BP on the protein S molecule (Amiral et al, Blood Coag. Fibrinol. 1994, 5:179–186 and Wolf et al., Blood Coag. Fibrinol. 1994, 5:187–192).

C4BP, which as stated above binds to protein S and thereby reduces the amount of free protein S circulating in blood, is composed of approximately seven identical α-chains, each of which contains a binding site for the complement protein C4b, and one single β-chain. The α-chains are linked in their C-terminal regions to each other and in addition to the single β-chain. These seven α-chains and the single β-chain of the C4BP molecule are arranged like wheel-spokes to form a spider-like molecular structure (Dahlbäck and Stenflo in The molecular basis of blood disease, eds Stammatoyannopolous et al. WB Saunders 1994, p 599–627). The protein S binding site is known to be located on the single β-chain and very recently (Härdig and Dahlbäck, J. Biol. Chem. 1996, Volume 172, p. 20861–20867) the entire protein S binding site has been localized to the extreme N-terminal SCR-module (SCR stands for Short Consensus Repeat, which is a protein module containing approximately 60 amino acid residues) of the β-chain. Although, this module has previously been proposed to contain the protein S binding site (Fernandez and Griffin, J. Biol. Chem. 1994, 269:2535–2540), it was not known before, that the entire protein S binding site is located in this first (extreme) SCR-module of the β-chain.

The knowledge of the complex formation between protein S and C4BP, has been used to develop antibodies, which are specific for the free form of protein S. Thus, attempts have been made to raise antibodies that bind specifically to the region of protein S that is involved in the binding of C4BP, which antibodies obviously would only bind to free protein S, since in the C4BP-bound form of protein S, such binding sites in protein S, which are specific for these antibodies, are already occupied by C4BP. A prerequisite for development of antibodies with the said specificity is, however, specific knowledge of the C4BP binding site on the protein S molecule. Whereas this binding site has not been elucidated in detail in prior art, two areas in a large C-terminal module of protein S designated SHBG have been claimed to be involved. The first report suggested residues number 605–614 of mature protein S to be involved (Walker, J. Biol. Chem. 1989, 264:17645–17648) whereas another region comprising residues 413–433 (Fernandez et al., J. Biol. Chem. 1993, 268:16788–16794) has more recently been suggested to be important for the binding of C4BP to protein S.

In WO 93/01209 monoclonal antibodies directed to specific regions of mature protein S, contemplated to be involved in C4BP binding, are disclosed, which antibodies are useful in diagnostic methods and systems for purifying or detecting free protein S. Protein S polypeptides comprising these specific regions are also disclosed. These regions differ, however, from the C4BP binding regions disclosed below.

Moreover, assays for free protein S based on immobilized monoclonal antibodies directed to free protein S, which are used as immobilized antibody in standard ELISA (Enzyme Linked Immuno Sorbent Assay) to capture free protein S in plasma, have been described in the literature and are also commercially available from Stago (Amiral et al., Blood Coag: Fibrinol. 1994, 5:179–186, and Wolf et al., Blood Coag. Fibrinol. 1994, 5:187–192). In such tests, plasma dilutions in buffer containing calcium are incubated in microtitre plates containing monoclonal antibodies specific for free protein S, and, subsequent to washing steps, protein S bound to the monoclonal antibodies can be detected with the use of a second mono- or polyclonal antibody directed to protein S. However, such assays are extremely expensive. Furthermore, the antibodies used in these tests are not well characterized and they have not been raised specifically against any region of protein S suggested to be involved in the binding of C4BP to protein S. Rather, these antibodies have been raised against the entire protein S molecule, whereafter antibodies having specificity for free protein S have been selected.

It is an object of the present invention to provide a simple and reliable assay for determination of free protein S in biological fluids. According to the present invention, this object is achieved with an assay wherein a ligand that binds specifically to free protein S is added to a biological fluid comprising protein S to form a protein S/ligand complex where-after the level of free protein S is measured as the protein S/ligand complex formed in said fluid, and wherein said ligand is comprised of at least part of the C4b-binding protein (C4BP), C4BP being a naturally occurring ligand for free protein S, or a compound comprising an amino acid sequence homologous or analogous to the protein S binding site of C4BP or an amino acid sequence having essentially the same protein S binding properties as C4BP.

More specifically, the present invention is concerned with a method as defined in claim 1.

In accordance with a suitable embodiment of the present invention, the said ligand binding to protein S is derived from C4BP per se and comprises either the entire protein or a (poly)peptide fragment thereof having appropriate protein S binding capacity. Suitably, this fragment comprises the entire, or substantially the entire, protein S binding site of C4BP.

Although, it is well known that C4BP is a natural ligand that binds to protein S, prior to the present invention no one has suggested use of C4BP per se, or a fragment thereof, as a tool to measure in a biological fluid sample, the level of free protein S in presence of protein S bound as PS:C4BP in a test primarily based only on formation of a complex between free protein S and C4BP or appropriate fragments thereof.

According to the present invention it has, however, quite unexpectedly been found that C4BP can be used as a reagent component in an assay as disclosed herein for determining free protein S, since, unlike most proteins, C4BP is quite stable over time and is comparatively insensitive to heat. Moreover, the dissociation rate of the complex formed is sufficiently slow to enable measurement thereof, both qualitative and quantitative.

In connection with the present invention, the term "ligand" is used to designate a molecular structure comprising an amino acid sequence that binds to an amino acid sequence of a receptor molecule, e.g. a protein peptide, polypeptide or the like, to form a molecular complex. In the present case, the receptor is comprised of free protein S. Thus, a ligand of the present invention can be comprised of an antibody paratope or a molecule comprising an amino acid sequence defining an antibody paratope, said molecule e.g. being an antibody or a fragment thereof.

According to one embodiment of the invention, the entire C4BP molecule, suitably in purified form, is used per se as a ligand to form a complex with free protein S, whereafter the complex formed, i.e. PS:C4BP, is measured in accordance with well known technique. It is of course necessary that this PS:C4BP complex formed in the assay can be distinguished from the PS:C4BP complex occurring naturally in blood. This can be achieved, e.g. by labelling and/or fixation of the C4BP used as ligand in the assay as is well known and will be disclosed more in detail further below.

Other embodiments of this invention are based on the knowledge of the exact localization of the protein S binding site in the C4BP molecule. Contrary to earlier reports, recently, this binding site has been found to occur in the extreme N-terminal SCR-module of the β-chain of the C4BP molecule.

Accordingly, the present invention is also concerned with fragments, i.e. short polypeptides, of the C4BP molecule which comprise the protein S binding site of the C4BP molecule and can be used as ligands binding to protein S for the same purpose as the entire C4BP molecule with use of the same assay formats. As is well known, such fragments can be derived from C4BP, e.g. by enzymatic digestion thereof. After determination of the corresponding amino acid sequence such fragments or polypeptides may conveniently be produced with the use of conventional synthetic methods, such as a solid-phase Merrifield-type synthesis. Methods based on recombinant technology could also be used.

Other embodiments of the invention are related to the knowledge of the localization of the C4BP binding site in native protein S. Based on this knowledge protein S polypeptides comprising the said binding site can be obtained and used to raise antibodies, monoclonal or polyclonal, which are specific for this binding site and, thus, for free protein S. Obviously, such antibodies can be used to determine free protein S in the presence of protein S bound to C4BP since such antibodies will not bind to protein S complexed with C4BP, the corresponding antigenic determinant or epitope in complexed protein S being already occupied by the C4BP molecule.

Thus, further embodiments of the present invention are concerned with the above protein S polypeptides (PS polypeptides) comprising the C4BP binding regions of native protein S and with anti-PS polypeptide antibodies specific for these regions and, thus, inhibiting the binding interaction between C4BP and PS. Such polyclonal or monoclonal antibodies would inunoreact with free protein S and have, thus, potential use both as diagnostic reagents and as a therapeutic agent.

Accordingly, the present invention is also related to therapeutic compositions comprising said antibodies, which bind to free protein S and, thus, prevent inactivation of protein S through PS:C4BP complex formation. The present invention is also related to a therapeutic composition comprising a polypeptide or a monoclonal antibody of the present invention in an amount sufficient to inhibit the binding of free protein S to C4BP, which polypeptide or monoclonal antibody binds to and blocks the binding sites for free protein S comprised in C4BP, and a pharmaceutically acceptable carrier, excipient or diluent.

Still further embodiments of the present invention are concerned with diagnostic systems, suitably in kit form, for assaying in accordance with the present method, free protein S in a biological fluid, said systems comprising as separately packaged reagents, a ligand of the present invention and at least one further reagent, such as indicating means, buffer, etc, required to perform the assay. Suitably, these systems comprise all reagents necessary to perform the assay. Usually, instructions for use of the packaged reagents are included in these systems.

The present diagnostic systems and methods for measuring free protein S can be designed in a variety of conventionally used formats, preferably as direct immunoassays, such assays being based on the specific binding interactions between the C4BP binding region of protein S on one hand, and C4BP or fragments thereof or polypeptides comprising an amino acid sequence homologous or analogous to the protein S binding site of C4BP, or the present anti-PS-polypeptide antibody paratopes, on the other hand.

According to a further embodiment, such systems and methods can also be used to purify free protein S from fluid samples. Thus, the present invention is also related to a composition for purifying free protein S from an aqueous solution comprising a ligand of the present invention operatively linked to a solid carrier, and to a method for purifying free protein S from an aqueous solution comprising contacting the said solution with the said composition to form a protein S/ligand complex bound to the solid carrier, separating said complex from said solution and releasing protein S from the said complex.

In the following, the invention will be disclosed more in detail with reference to suitable embodiments thereof. Even though, the present invention is primarily concerned with protein S of human origin, the invention could also be applicable to protein S of other, e.g. bovine, origin.

As stated above, the present invention is primarily related to the binding interactions between protein S and C4BP. More specifically, the present invention is related to the use of ligands specific for free protein S, which ligands can be used to capture free protein S, e.g. in assays for free protein S, the expression "free protein S" being used as a distinction from protein S circulating in the living body in the form of a complex with C4BP. Whereas one embodiment of the invention is merely based on use of the naturally occurring protein C4BP per se as ligand, other embodiments of the present invention are related to detailed knowledge of such interactions, viz. specific knowledge of the localization and/or the specific amino acid sequence of each of the interactive binding sites in protein S and C4BP, which are involved in complex formation between Protein S and C4BP. Thus, the invention is concerned with use of C4BP related ligands as well as use of antibodies or fragments thereof binding to free protein S.

1) Use of Ligands Comprised of or Derived From C4BP

With respect to ligands comprising at least part of or the entire site of C4BP that binds to native protein S, although use of the entire C4BP molecule is convenient and constitutes a suitable embodiment of the present invention, advantages can also be expected to be achieved by use of fragments of C4BP, which fragments comprise the specific amino acid sequence, or at least part thereof, that binds to protein S. It has been shown recently (loc. cit.) that in C4BP, the native protein S binding site appears in the extreme (first) SCR-module of the β-chain of the C4BP molecule. Thus, fragments which could be used as ligands in accordance with the present invention could be comprised of the intact β-chain of the C4BP molecule or fragments of this chain, comprising or consisting essentially of the said N-terminal SCR module. Use of such polypeptide fragments instead of the entire protein could be advantageous with respect to ease of preparation of the ligand and improved affinity could be achieved if such fragments are used as ligands in the present method for measuring free protein S.

As mentioned above, such fragments could be prepared by means of conventional peptide synthesis or methods based on recombinant technology, whereas use of C4BP per se usually encompasses isolation of C4BP from plasma in the form of the PS:C4BP complex, separation of C4BP from protein S and further purification. Appropriate fragments of C4BP, could also be derived from blood, for instance by enzymatic cleavage of C4BP obtained from blood, as disclosed above.

Moreover, use of recombinant technology opens up possibilities to design C4BP-like ligands having properties, which make such ligands specifically useful as catching ligands for free protein S. Thus, with use of recombinant technology, a hybrid molecule between the two types of chains, i.e. the α-chain and the β-chain, of the C4BP has been produced. In this construct, the extreme N-terminal SCR of the β-chain is replacing the corresponding module of the α-chain. The recombinant product obtained is a C4BP-like molecule having multiple disulphide-linked subunits, each of which contains a protein S binding site.

Even though it is possible to design C4BP-like molecules which could be very efficient as catching ligands in assays for free protein S, suitable embodiments of the invention are based on use of the entire C4BP molecule or, rather, C4BP species comprising the β-chain, i.e. C4BPβ, as ligands in such assays. Since the binding site on C4BPβ binds protein S with very high affinity ($K_D$=0.1 nM) in the presence of physiological calcium concentrations, the association rate constant in the presence of calcium ions being high (almost $10^5$ $M^{-1}$ $s^{-1}$) and the dissociation rate constant being low (approximately $5 \times 10^{-4}$ $s^{-1}$), C4BPβ (containing an unoccupied protein S binding site on the β-chain) is a highly specific and efficient ligand for free protein S and is able to specifically bind to free protein S in a solution containing both free protein S and PS:C4BP complexes.

It is, of course, essential that C4BP used as ligand in the present assay is substantially comprised of C4BP species containing the β-chain and, thus, the protein S binding site. This means that C4BP used in the present method is substantially comprised of its major isoform C4BPβ having seven α-chains and one β-chain as stated above, and that its minor isoform lacking the β-chain is absent or present in a low proportion.

In accordance with a suitable embodiment of an assay for free protein S of the present invention, C4BPβ is immobilized on a carrier, e.g. a microtiter plate, and is contacted, i.e. incubated, with a solution containing both free protein S and PS:C4BP complex to specifically bind to and, thus, extract free protein S from said solution, whereafter protein S, which is bound to the immobilized ligand, can be detected with mono- or polyclonal antibodies specific for protein S.

The high association rate constant in the presence of calcium allows very short incubation times to be used for this primary capturing. Suitably, a few washing steps are performed prior to the incubation with the said mono- or polyclonal antibodies. In principle, any antibody specific for protein S may be used. However, according to a suitable embodiment of the present method a monoclonal antibody is used, which has some unique properties, which makes it most suitable. This antibody, which is designated HPS54, has been characterized (Dahlbäck et al., J. Biol. Chem. 1990, 265: 8127–8135) and possesses unusually high affinity for protein S. Its epitope is located in the first EGF-like domain of protein S, i.e. it is distinct from the binding site for C4BPβ, which is located in the SHBG region, and calcium is required to achieve the high affinity of the binding of the said antibody to protein S. These unique properties make this antibody a suitable reagent to detect the protein S, which has been retained by the immobilized C4BPβ. To enable detection of protein S bound to the immobilized ligand, which protein S/ligand complex also carries bound HPS54 monoclonal antibody, HPS54 is either directly labelled to enable detection thereof or detected with secondary steps, such as secondary antibodies against this monoclonal antibody.

The method disclosed above using C4BP as a ligand is only given to illustrate the invention. The invention is not restricted to this embodiment but there is an almost unlimited number of possible ways to use the described principle for measurement of free protein S and a number of different designs of the assay principle are possible. Thus, modifications and further embodiments of the invention are obvious for he skilled artisan.

2) Use of Ligands Comprised of Antibodies Specific For Free Protein S

According to the present invention, the ligands used to capture free protein S can also be comprised of antibodies specific for free protein S. Thus, the present invention is related to such antibodies which have been raised directly against a region of protein S, which has been found to be involved in the binding interactions between protein S and C4BP.

Such antibodies are obtained with the use of the present PS polypeptides comprising the said specific regions, said polypeptides being used to prepare an inoculum, which is used to obtain the antibodies having the desired specifity, e.g. by administration (immunization) of an appropriate animal.

These PS polypeptides comprise regions of mature protein S that differ from such regions of protein S, that in prior art have been suggested to be involved in the binding of C4BP.

In accordance with the present invention, the regions of protein S, which have been found to be involved in the binding of C4BP, and which, thus, when present in an antigen, e.g. a polypeptide, are potentially useful as immunogens or antigens to raise antibodies specific for free protein S, all include the amino acid residues 447–460 of mature protein S, represented by the formula SGIAQFHIDY NNVS.

In general terms, the present invention is, thus, concerned with PS polypeptides, said polypeptides comprising at least amino acid residues 447–460 of mature protein S. Optionally, said polypeptides may comprise additional N-terminal and/or C-terminal amino acid residues that differ from the corresponding flanking residues of protein S. The PS polypeptides could also comprise an N-terminal or C-terminal part of the 447–460 amino acid sequence and resp., additional N-terminal or C-terminal flanking residues corresponding to those of mature protein S, or could comprise the entire 447–460 amino acid sequence with additional flanking residues at both ends, which flanking residues correspond to those of mature protein S. Illustrative of such PS polypeptides are polypeptides comprising amino acid residues 439–460, 447–468, and 435–468, resp., (Table 1). The inventors have shown that synthetic polypeptides corresponding to the above sequences are capable of inhibiting protein S-C4BP interaction, whereas synthetic polypeptides corresponding to residues 405–437 and 595–628 (Table 1), which in prior art have been suggested to be involved in the binding of C4BP, did not show any inhibitory effect, not even if used in excess (2000×) over protein S. Thus, the present polypeptides comprise an amino acid residue sequence corresponding to the amino acid residues 447–460 of mature protein S and optionally additional flanking residues of mature proteins at one or both ends but suitably do not extend beyond amino acid residue 438 of mature protein S in their N terminus or amino acid residue 526 of mature protein S in their C terminus. Apart from being derived from protein S, the present polypeptides can also be prepared with conventional polypeptide synthesis.

The above amino acid numbering of protein S corresponds to the conventional numbering used e.g. in Lundwall, Å. et al., Proc. Nat'l Acad. Sci. USA, vol. 83, p. 6716–6720 (human protein S) and Dahlbäck, B. et al., Proc. Nat'l Acad. Sci. USA, vol. 83, p. 4199–4203 (bovine protein S), which references disclose the cDNA and the amino acid sequence of protein S.

Accordingly, a suitable embodiment of the present invention is directed to antibodies, polyclonal or, preferably, monoclonal, that have been raised against the above PS polypeptides and, thus, are capable of immunoreacting with the above amino acid residue sequences of protein S, which have been found to be involved in high affinity binding of C4BP to free protein S. As explained above, such antibodies will be specific for free protein S and will not bind to protein S complexed with C4BP.

The present antibodies are referred to as anti-PS antibodies and are characterized by immunospecificity for free protein S. In addition, they can be expected to be capable of inhibiting binding of protein S to C4BP and, thus, to be useful as a drug to enhance the amount of free protein S in blood.

Suitable anti-PS antibodies of the present invention are capable of immunoreacting with a polypeptide comprising the amino acid residues 447–460 of mature protein S, said antibodies also immunoreacting with the same amino acid sequence in free protein S.

The present antibodies can be produced in accordance with commonly known methods with use of commercially available protocols. Generally, an animal, preferably a mammal, is inoculated, e.g. injected, with a PS polypeptide of the present invention comprising amino acid residues 447–460 of mature protien S and used in an amount sufficient to induce production of antibodies in said animal. Subsequently, the antibodies thereby produced are collected from the animal, suitably in serum, ascites or some other body fluid, or an antibody-producing organ, such as spleen, is used to produce antibodies with recombinant technique.

Those antibodies, that have the desired immunospecificity are preferably isolated from e.g. the body fluid, suitably by immunoaffinty chromatography, or with other well known techniques. If immunoaffinity chromatography comprising solid phase-affixed inmmunizing polypeptide is used to purify the antibodies, their specifity could be enhanced. Such immunoaffinity chromatography comprises contacting the antibodies with solid phase-affixed immunizing polypeptide, a solid phase-affixed immunocomplex being formed and, subsequent separation of the antibodies from this immunocomplex.

Since the PS polypeptides used to immunize the animal are short polypeptides, they are preferably included in the inoculum linked to a carrier to form a conjugate. Use of such conjugates are preferred for peptides comprising about 35 amino acids or less. Suitable carriers are well known in the art and comprise keyhole limpet hemocyanin (KLH), hemocyanin from horseshoe crab (Limulus polyphemus), edestin, thyroglobulin, albumins and the like.

To assist in linking the polypeptide to the carrier, the polypeptide may comprise additional amino acid residues added to the amino- or carboxy-terminus of the polypeptide. Suitably, cystein residues are added and a carrier is used comprising free cystein residues so that a polypeptide/carrier conjugate is obtained by the formation of disulphide bonds. Such added cystein residues may also assist in performing the above immunoaffinity purification, e.g. by binding the immunizing polypeptide comprising added cystein residues to an affinity matrix comprising free cystein residues, e.g. ThiolSepharose® from Pharmacia Fine Chemicals.

The present antibodies can be polyclonal or monoclonal, monoclonal antibodies usually being preferred. The expression "antibody" is intended to refer not only to the entire antibody but also to appropriate fragments thereof. Monoclonal antibodies contain only one single species of antibody combining site, or paratope, capable of immunoreacting with a particular epitope. However, a monoclonal antibody may comprise more than one specific antibody combining site, such antibodies being polyspecific, e.g. bispecific. Suitably the present monoclonal antibodies are monospecific and comprise a single paratope specific for the present PS polypeptides and are, thus, also specific for free protein S.

The preparation of monoclonal antibodies is well known in the art and was first disclosed by Koehler and Milstein, Nature, 256: 495–497, 1975. As disclosed in this reference, monoclonal antibodies are produced by clones of one single cell designated hybridoma. These hybridomas are formed by fusion of an antibody-producing cell, usually lymphocytes, with a myeloma or other self-perpetuating cell line and they secrete antibodies into the supernatant of the hybridoma cell culture. To produce the present hybridomas, lymphocytes are used, which have been collected from an animal previously hyperimmunized with the present PS polypeptide as antigen. The present invention is also related to hybridoma cells and cell cultures containing such hybridoma cells that produce a monoclonal antibody of present invention.

Preferably, the polyclonal or monoclonal antibodies of the present invention immunoreact with the present PS polypeptides disclosed in the experimental part of this disclosure, and, thus, immunoreacts with free protein S with high specifity.

In accordance with a suitable embodiment of the present invention such antibodies can be used in a test system, e.g. a diagnostic kit, which is intended to be used in an ELISA format to detect the quantity of free protein S in a fluid sample, such as blood, serum, or plasma, wherein this antibody is bound to a solid phase and an enzyme-antigen conjugate is used to detect and quantify the amount of antigen, i.e. free protein S, in a sample.

As stated above, the present antibodies and the C4BP related ligands can be used in a diagnostic system for assaying free protein S. In accordance with the present invention, such systems usually also include indicating means to facilitate determination, qualitative or quantitative, of the receptor/ligand complex formed in the assay of the present invention. Such indicating means may be used in addition to fixation of the ligand to a substrate, or as an alternative enabling assays of said complex in free form, i.e. not bound to a solid carrier, matrix, or the like.

Such indicating means or labels are comprised of single atoms or molecules, that can be linked to or incorporated in the present ligand, or used separately, and that are involved, either directly or indirectly in the production of a detectable signal to indicate the formation of the present receptor/ligand complex. Additional reagents may be required, e.g. in connection with enzyme labels, the corresponding substrate being required to visualize the signal. Useful indicating means or labels are well known within this field of art and e.g. include chromogenic, fluorogenic and cheriluminogenic labels, suitably fluorogenic labels, such as fluorescein isocyanate (FIC). Other labels, which can be used, are enzymes, such as horseradish peroxidase (HRP), and radioactive isotopes, such as $^{125}$I.

Suitably, the present ligand is affixed, e.g. by absorption, to a solid matrix. Useful solid matrices are well known in the art and are composed of water insoluble materials, such as cross-linked dextran available under the trademark Sephadex from Pharmacia Fine Chemicals; agarose; beads of polystyrene having a diameter of about 1 $\mu$m to about 5 mm and available from Abbott Laboratories of North Chicago, Ill.; polyvinyl chloride, polystyrene, cross-linked polyacrylamide, nitrocellulose- or nylon-based webs, such as sheets, strips or paddels; or tubes, plates or the wells of a microtiter plate, such as those made from polystyrene or polyvinyl chloride.

The reagent components of the diagnostic system described herein can be provided in solution or as a liquid dispersion. However, suitably, they are provided as a substantially dry powder, preferably in lyophilized form. If an enzyme is used as indicating means, the corresponding substrate can also be provided in a separate package of the system. A solid support, such as a microtiter plate as mentioned above and one or more buffers can also be included as separately packaged elements in the present diagnostic system.

Suitable embodiments of the present invention are explained in more detail in the illustrative examples and with reference to the accompanying drawings.

EXAMPLE 1–4

Figure 1:
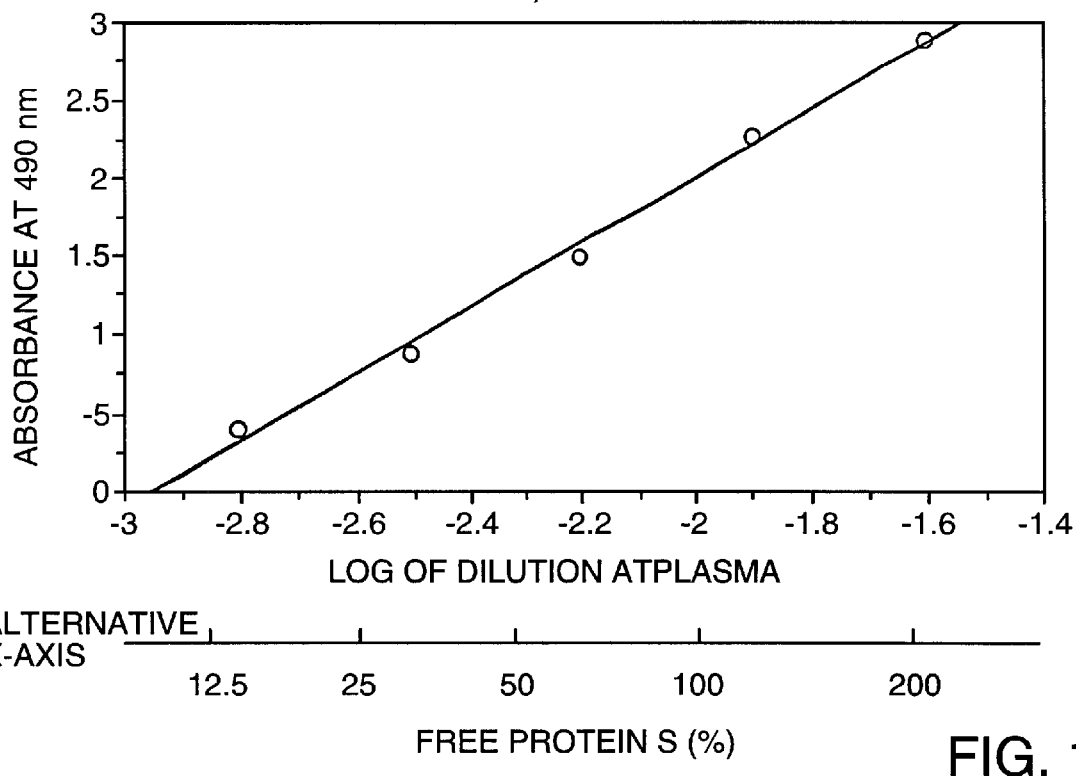
FIG. 1 shows a standard curve obtained with normal plasma dilutions (1:40–1:640). Absorbance values at 490 nm ($A_{490}$) are plotted against the logarithmic dilution values. As an alternative, $A_{490}$ values are plotted against the level (%) of free protein S (lower x-axis).

In these examples, a specific assay for free protein S in accordance with the present invention is disclosed, wherein C4BP is used as a ligand, immobilized on a solid support, to catch free protein S in a plasma sample. As solid supports, microtiter plates were used.

Example 1

Preparation of Plates and Other Materials, Such as Reagents and Plasma Samples, Used in the Assay
A. Preparation of Microtiter Plates Containing Immobilized C4BP As ligand, a species of C4BP containing the protein S binding β-chain and designated C4BPβ was immobilized in wells on microtiter plates (Maxisorb from NUNC. Denmark) using the following standard procedure: 10 $\mu$g/ml purified C4BP in 50 mM carbonate buffer, pH 9.6, 50 µl/well—overnight incubation. The wells were washed three times with 50 mM Tris-HCl, 0.15 M NaCl, pH 7.5 (TBS), containing 0.1% Tween (TBS-washing buffer) and then incubated at room temperature for 30 minutes with 1% bovine serum albumin (BSA) diluted in TBS. The plates were then washed with TBS-washing buffer and stored in the refrigerator. Under these conditions, the performance of the plates in the free protein S assay was found to be acceptable for at least 5 weeks.

B. Preparation of C4BPβ Used as Ligand Immobilized in Section A

C4BPβ was first isolated from human plasma in the form of the protein S-C4BP complex. Thereafter, this complex was dissociated and C4BPβ was separated from protein S by gel filtration chromatography in 3M guanidine-HCl and C4BPβ was further purified in a monoclonal antibody affinity chromatography process. In accordance with this process, the product obtained is predominantly C4BPβ although a minor proportion of C4BP-species lacking the β-chain might be separated together with C4BPβ. The isolation of C4BP has been described previously (Dahlbäck, Biochem. J. 1983, 209: 847–856 and modified in Hillarp and Dahlbäck, J. Biol. Chem. 1988 263: 12759–12764).

C. Preparation of Plasma Samples For Standard Curve

A pool of normal citrated human plasma (from approximately 40 donors) was used to construct the standard curve. The plasma was diluted 1:40–1:640 in the same buffer as was used for the patient samples and handled in the same way as the patient samples.

D. Preparation of Protein S Depleted Plasma

Normal human plasma (20 ml which was anticoagulated with tri-sodium citrate in a standard manner) was mixed with an affinity matrix for protein S, the matrix being 15 ml HPS54-Sepharose (Sepharose containing immobilized monoclonal antibody HPS54), and incubated for 2 hours at 4° C. during gentle mixing. The protein S depleted plasma was collected by centrifugation and stored at −70° C.

Example 2
Assay Procedure For Establishment of Standard Curves and For the Assay of Patient Plasma The following assay procedure was used to determine free protein S in normal plasma dilution samples to construct a standard curve. The same procedure is used for the assay of patient plasma samples.

Assay Procedure

Aliquots (50 µl) of the sample to be analyzed (for patient plasma usually 1:100 dilutions of plasma, the buffer for dilution being TBS containing 1% BSA, 2 mM calciumchloride and 1 mM benzamidine) were added to the wells of C4BP-microtiter plates and incubated at room temperature for 30 minutes. The wells were then washed with TBS-wash-ing buffer and biotinylated monoclonal antibody HPS54 (diluted 1:1000, corresponding to about 0.1–1 µg/ml, in TBS containing 1% BSA, 2 mM calcium chloride) was added. Unbound HPS54 was washed away with 3×TBS-washing buffer. Peroxidase-conjugated streptavidine (from Dakopatts AS and prepared according to the manufacturers instructions and diluted 1:2500) (50 µl/well) was added and incubated 15 minutes at room temperature before unbound complexes were washed away with 3×TBS-washing buffer. Aliquots (100 µl/well) of the peroxidase substrate OPD (1,2-ortho-phenylene diamine in the form of 2 mg tablets from Dakopatts A/S) at 1.5 mg/ml in 0.1 M citric acid-phosphate buffer, pH 5.0 (prepared according to instructions from Dakopatts) was added together with $H_2O_2$ (0.015%).

After exactly 5 minutes, the reaction was stopped by 100 µl/well of 1 M $H_2SO_4$ and the absorbance was measured at 490 nm.

To establish a standard curve, the absorbance values obtained above for the plasma dilution samples were plotted on the y-axis against the plasma dilutions (1:40–1:640) on a logarithmic x-axis in a standard fashion (FIG. 1). The patient samples were tested at 1:100 dilution and the absorbance obtained was used to calculate the amount of free protein S. The values were expressed as % of the free protein S present in normal plasma. The values in % of free protein S can be read directly on the alternative (lower) x-axis in FIG. 1. The assay can also be calibrated against an international standard having an assigned protein S level or against a standard of purified protein S.

The final protocol of the assay of Example 2 was determined after careful testing of conditions for the various steps. Indeed, each step was evaluated with the goal of finding the fastest assay without compromising the accuracy of the test. Thus, the procedure described above was the result of an integrated evaluation of the influence of various dilutions, temperatures and incubation times and represent just one of many possible combinations which give a satisfactory assay procedure. Conditions preferred at present and other suitable conditions are obvious from the following.

Incubation Times For Plasma Dilutions in C4BP-microtiter Plates

Room temperature allowed faster binding of free protein S to the immobilized C4BP and was therefore used rather than incubation in the refrigerator. Three different plasma dilutions (1:60, 1:120, and 1:240) were incubated between 30 minutes and 5 hours before the rest of the assay was completed. The 1:60 dilution gave maximum response (high absorbance) already after 1 hour, the 1:120 dilution after 2 hours and the 1:240 dilution reached its maximum after 4–5 hours. For practical purposes, 30 minutes incubation and a 1:100 patient plasma dilution, were preferred.

Incubation Time and Dilution For Biotinylated HPS54

Dilutions of the biotinylated monoclonal antibody (1:500–1:4000) were incubated for 15 and 30 minutes in the assay. The higher dilutions gave absorbance values almost as high as the lower dilutions. A 1:1000 dilution and 15 minutes incubation were, therefore, preferred.

Incubation Time and Dilution of the Peroxidase Conjugated Streptavidine and Also the Substrate Development Time In a manner similar to that described above, it was established that the incubation time and dilution factor for the enzyme preferably would be 1:2500 dilution and 15 minutes incubation time. The substrate conversion time would preferably be 5 minutes.

The present assay performed essentially as disclosed in Example 2 is a reliable test, which is easy to work. The fast on-rate for protein S to its binding site on C4BP allows short incubation times. The slow off-rate of protein S from C4BP allows performance of the washing procedures and subsequent steps including addition of monoclonal antibody directed against bound protein S, addition of the enzyme conjugate and finally the substrate for the enzyme. Moreover, the on-rate has been found to be faster and the off-rate slower in the presence of calcium. For this reason, the buffer used in the assay preferably contains calcium. This is probably an important factor which contributes to the excellent performance of the assay. Furthermore, by optimizing each step, it is possible to reduce the time required to perform the assay. Thus, it is possible to design a fast assay, which can be performed within 2 hours. In addition, the assay is suitable for automatization and allows the processing of a large number of samples.

Example 3
Specificity and Sensitivity of the Assay Using C4BP as Ligand

A. Specificity of the Assay For Free Protein S

To test the specificity of the assay for free protein S, two different experiments were performed. In the first experiment, protein S depleted plasma was tested in accordance with the present assay and found to contain undetectable levels of free protein S. This indicated that the assay was not detecting any other component of plasma. In reconstitution experiments, i.e. after protein S replenishment of protein S depleted plasma, the protein S recovery was between 80 and 90%. Thus, the addition of three concentrations of highly purified protein S to protein S depleted plasma (20, 10, and 5 µg/ml) gave in the assay approximately 17.5, 8.5 and 3 µg/ml, resp., provided that the 100% level of normal plasma corresponds to 10 µg/ml of free protein S, which has been suggested in the literature (Malm et al "Changes in the plasma levels of vitamin K-dependent protein C and S and C4b-binding protein during pregnancy and oral contraception", Brit. J. Haematol. (1988) 68:437–443). Thus, within experimental error, this experiment supports the conclusion that the assay is specific for protein S and suggests that it is also specific for the free form of protein S. To prove this latter point, C4BP was added to human plasma (in amounts which would theoretically give 1:1, 2:1 and 10:1 molar ratios of C4BP to free protein S in plasma—again assuming an amount of 10 µg/ml of free protein S in normal plasma) and incubated for 1 hour at 37° C. The idea with this experiment was that C4BP can bind free protein S and that this would lead to a drop in the measured amount of free protein S. This was also found to be the case, as the addition of a two-fold molar excess of C4BP compared to free protein S resulted in a 90% drop in free protein S. The specificity of the assay for free protein S was also further proven by the comparison of the result of the present assay with those obtained with two prior art assays for free protein S. This comparison is described in more detail in Example 4. The coefficient of variation of the assay was found to be 8.5% for inter-assay (n=15) and 7% for intra-assay (n=20) determinations.

B. Sensitivity of the Assay

When the assay was performed according to the protocol described in Example 2, the 1:100 dilution represented 100% which corresponds to approximately 100 µg/ml of free protein S (assuming an amount of 10 µg/ml free protein S in undiluted plasma). The assay allowed accurate quantification of free protein S levels between 15 and 250% (when using a plasma dilution of 1:100) which corresponds to 15–250 ng/ml of free protein S. By using some other plasma dilution, e.g. 1:5 or 1:10, the assay can be even more sensitive and measure levels as low as 1% which may be of interest in certain situations, e.g. in prenatal diagnosis to determine if a child is homozygous deficient in protein S.

Example 4
Comparison With Prior Art Assays For Free Protein S

The performance of the present assay for free protein S in accordance with the protocol of Example 2 was compared with those of two other assays for free protein S. Assay 1 was a home-made radio immuno assay (RIA) which is very well characterized and has during some time in international evaluations been considered to be a gold-standard. The assay is previously described by Malm et al, "Changes in the plasma levels of vitamin K-dependent protein C and S and C4b-binding protein during pregnancy and oral contraception", Brit. J. Haematol. (1988) 68:437–443. In this assay, total and free protein S are measured with a standard RIA procedure which includes radio-labelled protein S and a polyclonal protein S antiserum. Total protein S is measured directly in plasma dilutions, whereas free protein S is measured after precipitation of the protein S-C4BP complexes in plasma with 5% polyethylene glycol (PEG) 6000. The assay is time-consuming (usually more than two days) and laborious. The second assay, which was used for comparison is a commercially available ELISA which uses two monoclonal antibodies, one of which is specific for free protein S and is used as catcher antibody (i.e. for the same purpose as C4BP in the assay of Example 2). The assay is available from Stago and is described in a publication by Amiral and colleagues, "New direct assay of free protein S antigen using two distinct monoclonal antibodies specific for the free form". Blood Coagulation and Fibrinolysis (1994) 5: 179–186.

A. Patient Groups Which Were Compared

1. Plasma samples (n=220) from the Coagulation laboratory at the University Hospital in Malmö which had been analyzed with the RIA for evaluation of their protein S levels. The patients were mostly patients with a history of deep venous thrombosis.

2. Protein S deficient family members. A number of protein S deficient families have been evaluated with the RIA at the Coagulation laboratory mentioned above and the results have been published by Zöller and colleagues, "Evaluation of the relationship between protein S and C4b-binding protein isoforms in hereditary protein S deficiency demonstrating type I and type III deficiencies to be phenotypic variants of the same genetic disease", Blood (1995) 85: 3524–3531. From these families, 150 plasma samples were randomly chosen and tested with the assay of Example 2 as well as with the Asserachrome assay for free protein S from Diagnostica Stago. In addition, the results were compared with results obtained with the in-house RIA.

3. Plasma samples from patients (with or without protein S deficiency) receiving longterm oral anticoagulation treatment with vitamin K-antagonists (warfarin); 61 samples from patients with thrombotic episodes were included, 23 of the patients were from families with protein S deficiency.

B. Results of the Comparative Tests

Figure 2:
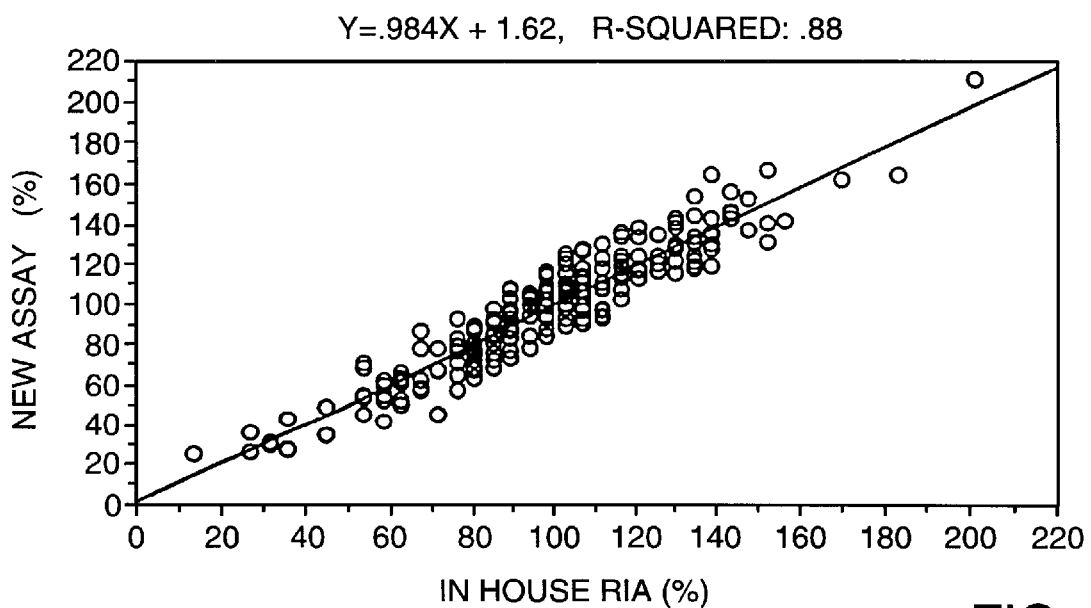
FIG. 2 shows the results from a linear regression analysis. Values (%) obtained with the assay of Example 2 are plotted (on the y-axis) against values (%) obtained with an in-house RIA (on the x-axis).

1. The values obtained with the assay for free protein S disclosed in Example 2 were compared with the results obtained with the in-house RIA for free protein S. Both assays expressed the free protein S as % of the normal level of free protein S. From a linear regression analysis (FIG. 2), it was obvious that the two assays measured the same parameter and that they correlated well. The linear regression equation was y=0.984x+1.62; $R^2$=0.88 (R=0.94) P=0.0001. There were no outliers.

Figure 3:
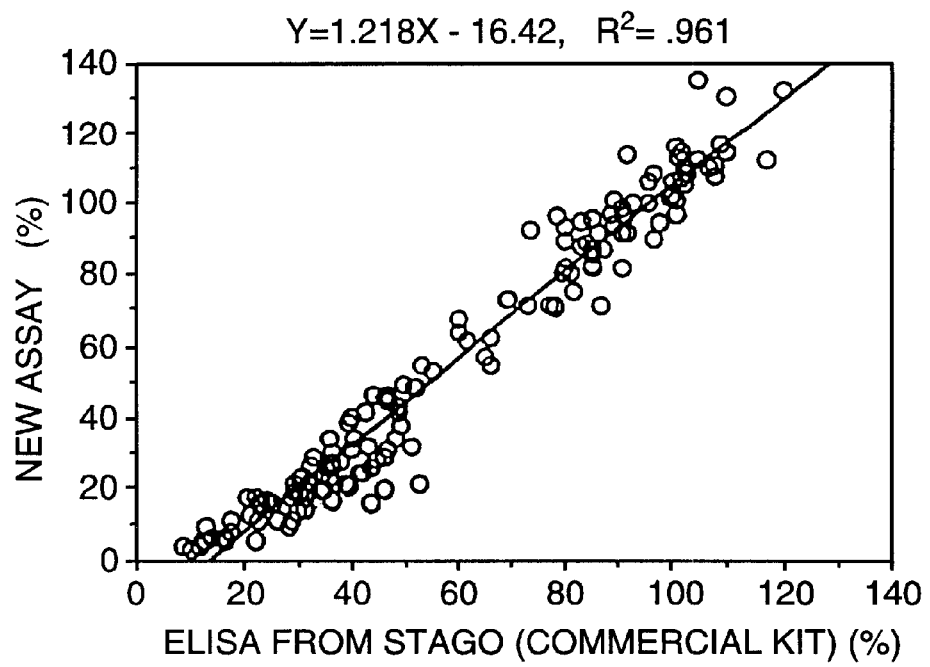
FIGS. 3 and 4 show the correlation between values obtained with the assay of Example 2 (y-axis) and (on the x-axis) values obtained with commercial ELISA according to Stago (FIG. 3) aid with an in-house RIA (FIG. 4).
Figure 4:
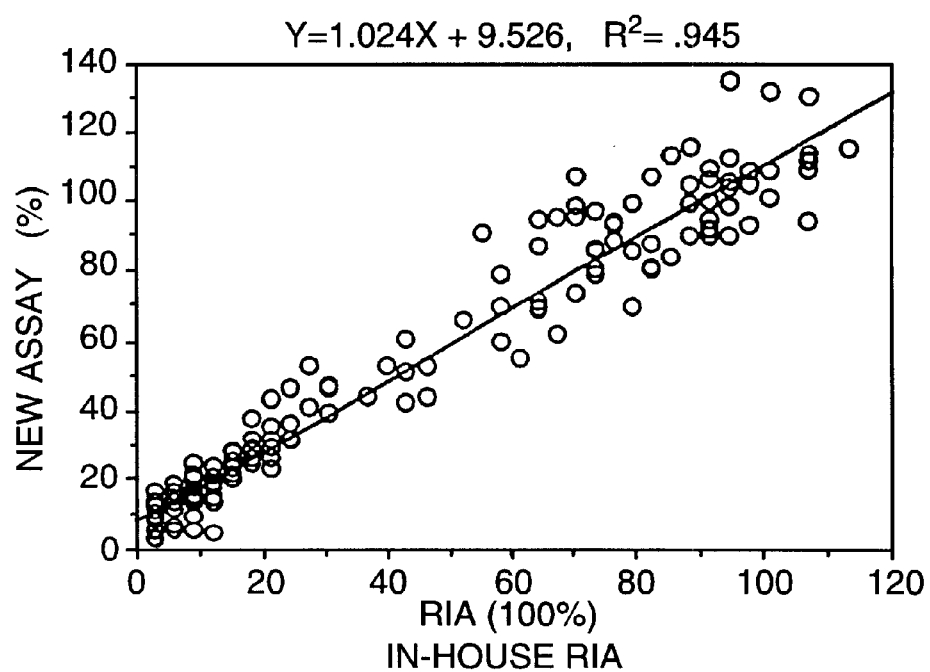

2. Plasma samples (n=155) from individuals belonging to families with known protein S deficiency were tested with the three assays, i.e. the present assay of Example 2, the Stago assay and the in-house RIA. As illustrated in FIGS. 3 and 4, the correlations were excellent with $R^2$-values close to 0.95. All three assays measured the same parameter and were equally efficient in identifying individuals with suspected protein S deficiency. When compared to the Stago assay, the regression equation was y=1.218x–16.42 (the present assay on x-axis) which indicates a steeper dose-response curve with the present assay. Moreover, the present assay was more accurate for low values and gave results as low as close to 0% whereas in the Stago assay, none of the samples gave values below 5%. There was a considerable negative intercept of –16.42. When the present assay instead was compared with the in-house RIA, the intercept was positive (+9.526) (regression equation y=1.024x+9.526). In this comparison, the slope was close to 1.

3. The correlations obtained with the plasma samples from patients receiving oral anticoagulation were acceptable. In tests involving comparison with RIA, the regression equation was y=0.88x–2. $R^2$=0,86 and y denotes values from RIA.

From the above Examples 1–4, it is obvious that C4BP is feasible as a cathing ligand in assays for free protein S, said assay having an accuracy at least as high as prior art assays. Moreover, the present assay involving C4BP is less time-consuming and is easy to perform by routine.

The following Example 5 is related to embodiments of the present invention using antibodies as catching ligands, which antibodies immunoreact specifically with the binding site for C4BP in protein S and also with the protein S related polypeptides of the present invention. In Example 5, the binding of the present polypeptides to C4BP and their capability to inhibit binding of C4BP to protein S and, thus, protein S/C4BP interactions, are investigated and compared to polypeptides outside the scope of the present invention (inclusive of some prior art polypeptides). The present polypeptides, which have the above mentioned properties, will be feasible as immunogens or antigens to produce the present antibodies, which can be used as catching ligands in assays of the present invention.

Example 5
Protein S Related Polypeptides
A. Peptide Synthesis and Purification

The linear protein S related peptides listed i Table 1 were synthesized on a MilliGen 950 Plus synthesizer as a "continous flow peptide synthesis" using Fmoc chemistry with active esters, viz. pentafluorophenyl esters. The peptides are hereinafter referred to by their polypeptide designations as listed in Table 1. Also listed in Table 1 are the amino acid residues of each peptide and the corresponding amino acid sequence identification numbers of mature protein S. The first amino acid in the synthesis (the C-terminal amino acid) was coupled to the resin PEG-PS Support™ from Millipore (polyethylene glycol polystyrene). After synthesis, the resin was rinsed and dried. The peptide was released from the resin by cleavage for 2 hours under $N_2$-gas in the darkness using 92–95% TFA containing different scavengers depending on the amino acid composition of the peptide. The resin was removed by filtering and washed with concentrated TFA. After concentration, the peptide was precipitated and washed 4 times in cold diethyl ether. The ether was evaporated and the peptide was dissolved in 0.1% TFA/$H_2O$ (or in 50–75% acetic acid for the SL1, SL2, SL4, SL6 and SL7 peptides that were difficult to dissolve in 0.1% TFA). The peptide was purified on a HPLC (Waters 600E System Controller, Waters 486 Tunable Absorbance Detector on a C8 column (Kromasil 5, 100A C8, 250 mm×21.2 mm) using a linear gradient of A) 0.1% TFA/$H_2O$ and B) 0.1% TFA/ 80% acetonitrile/$H_2O$. The peptide was concentrated by speedvac and lyophilization.

B. Peptide Folding

The peptides BD4 and BD6 were reduced (in 0.1 M Tris pH 8.3 with 0.1 M DTT and 6M guanidine-HCl, for 2 hours at room temperature at a peptide concentration of 10 mg/ml) prior to HPLC purification (as described above). After purification they were folded to form a disulfide bond between the two cysteines in each peptide (in 0.1 M Tris pH 8.3 with 1 mM EDTA, 3 mM cysteine-HCl and 0.3 mM cystin under $N_2$ gas for 16 hours at room temperature at a peptide concentration of 0.1 mg/ml). The peptides were subject to a second HPLC purification (as above) after folding.

C. Chemicals

All chemicals were of highest grade commercially available. Buffers and all other solutions were autoclaved or sterile filtered prior to use. Sterilized labware was used throughout. The following abbreviations for autoclaved buffers are used in this Example: TBS=50 mM Tris, 0.15 M NaCl, 2 mM $CaCl_2$, pH set to 7.5 with HCl; TBS/Tween= TBS with the addition of 0.5% Tween; TBS/$NaN_3$=TBS with the addition of 0.02% $NaN_3$; HC=10 mM Hepes, 0.15 M NaCl, 3.4 M EDTA, 0.005% Tween 20, pH 7.4; PBS=0.1 M sodium phosphate buffer, pH 7.0 with 0.15 M NaCl. The sensorchips CM5 and amine coupling kit containing N-hydroxysuccinimide (NHS), N-ethyl-N'-(3-diethylaminopropyl)-carboxydiimide (EDC) and ethanolamine hydrochloride were from Pharmacia Biosensor AB (Uppsala, Sweden). The surfactant Tween 20 was from Riedel de Haen. NHS-LC-biotinylation kit was from Pierce (Rockford, Ill.). Chemicals for peptide synthesis were from Millipore.

D. Peptide Inhibition of the Protein S-C4BP Interaction in Microtiter Plates

Microtiter plates were coated with C4BP, 50 µl/well, 10 µg/ml in 0.075 M sodium carbonate buffer, pH 9.6. The plates were incubated over night at 4° C. and then washed with TBS, pH 7.5, containing 0.1% Tween 20. After quenching (TBS, pH 8.0 containing 0.05% Tween 20, 3% fish gelatine and 0.02% $NaN_3$, 100 µl/well, 30 minutes) and washing, increasing concentrations of the peptides (0.1–3000 mM) or plasma purified human protein S (0.13–1333 mM) in TBS containing 10 mM EDTA were added together with a trace amount of $^{125}$I-labelled protein S in a final volume of 50 µl and left at 4° C. over night. The wells were then washed and the amount of bound protein S detected using a γ-counter.

E. Peptide Inhibition of the Protein S-C4BP Interaction According to Surface Plasmon Resonance Studies The surface plasmon resonance studies were performed using a BIAcore™ apparatus from Pharmacia Biosensor

TABLE 1

Synthetic peptides

| Designation | Amino acid residue sequence | hPS seq. id. no. | |
|---|---|---|---|
| BD4 | LDGCIRSWNLMKQSASGIKEIIQEKQNKHCLVT | 405–437 | (SEQ ID NO: 1) |
| BD6 | YNGCMEVNINGVQLDLDEAISKNNDIRAHSCPSV | 595–628 | (SEQ ID NO: 2) |
| SL1 | KPENGLLETKVYFAGFPRK | 374–392 | (SEQ ID NO: 3) |
| SL2 | EKGSYYPGSGIAQFHIDYNNVS | 439–460 | (SEQ ID NO: 4) |
| SL3 | SDQQSHLEFRVNNLEKSTPLK | 527–550 | (SEQ ID NO: 5) |
| SL4 | DKAMKAKVATYLGGLPDVPFSAT | 567–589 | (SEQ ID NO: 5) |
| SL5 | LVTVEKGSYYPGSGIAQ | 435–451 | |
| SL6 | SGIAQFHIDYNNVSSAEGWHVN | 447–468 | |
| SL7 | LVTVEKGSYYPGSGIAQFHIDYNNVSSAEGWHVN | 435–468 | (SEQ ID NO: 7) |

AB. Immobilization of C4BP to the dextran coated gold surface of a sensorchip was performed at a flow rate of 5 μl/min, using HC as flow buffer. Equal volumes of 0.1 M NHS and 0.1 M EDC were first mixed, whereafter 30 μl of the mixture was flown over the sensorchip surface to activate the carboxymethylated dextran. C4BP was then injected over the sensorchip (40 μl of a 60 μg/ml solution in 10 mM NaOAc at pH 4.75), whereafter unreacted NHS-ester groups were blocked by 15 μl 1M ethanolamine (pH 8.5). The system was regenerated by addition of 15 μl 0.1 M HCl, which removes all non-covalently bound molecules. The immobilized amount of C4BP was 8000 RU. Protein S association was monitored with 50 nM human protein S in HC buffer in a continuous flow of 1 μl per minute during 45 minutes. The ability of each peptide to inhibit the protein S binding was studied by following the association to C4BP for mixtures of protein S and peptide. In BIAcore™, the total amount of bound material is measured, and the peptides are 25-fold smaller than protein S, inhibition of protein S-binding by peptide binding will drastically lower the observed response during the association phase. The percent protein S bound, X, was calculated as $$X = (S - 0.04\ S_{max})/0.96\ S_{max}$$

where S is the measured response and $S_{max}$ is the response obtained in the absence of peptide.

Figure 5A:
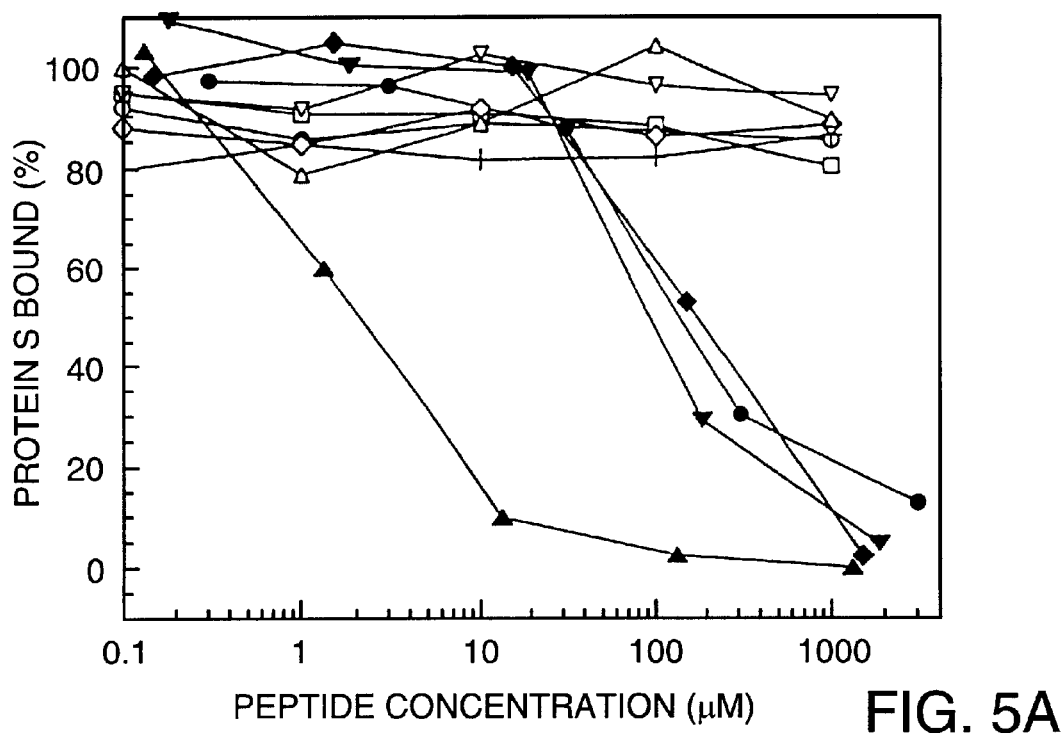
FIGS. 5A and 5B show peptide inhibition of protein S/C4BP interactions in an equilibrium binding assay (FIG. 5A) and in a surface plasmon resonance assay (FIG. 5B).

F. Experimental Results (1) Peptide Inhibition of Protein S-C4BP Interaction in an Equilibrium Assay As disclosed in Section D, the synthetic peptides were tested for their ability to displace binding of a $^{125}$I-labelled protein S tracer to immobilised C4BP (FIG. 5A). SL2, SL6 and SL7, i.e. the peptides of the present invention, were found to completely inhibit binding of the protein S tracer to C4BP, whereas none of the other peptides had any effect on the protein S/C4BP interaction. Half-maximum inhibition was seen at 100–200 μM of the three inhibiting peptides as compared to approximately 2 μM for plasma purified human protein S.

(2) Peptide Inhibition of the Protein S-C4BP Interaction According to a Surface Plasmonance Assay As disclosed in Section E, the ability of the synthetic peptides to inhibit the binding of human protein S to C4BP was also studied using surface plasmon resonance on a BIAcore™ system. For six of the peptides (SL1, SL3, SL4, SL5, BD4 and BD6), the same response was observed as with protein S alone, even when the peptides were in 2000-fold excess over protein S (100 μM peptide, 50 nM protein S). However, three peptides, SL2, SL6 and SL7, i.e. the peptides of the present invention, prevent the binding of protein S to C4BP with half maximum inhibition at 30–120 μM peptide concentration (FIG. 5B).

Thus, residues 447–460 are present in all three peptides with inhibitory action, viz. the peptides of the present invention, but are absent in the peptides lacking inhibitory action in the above tests.

Figure 5B:
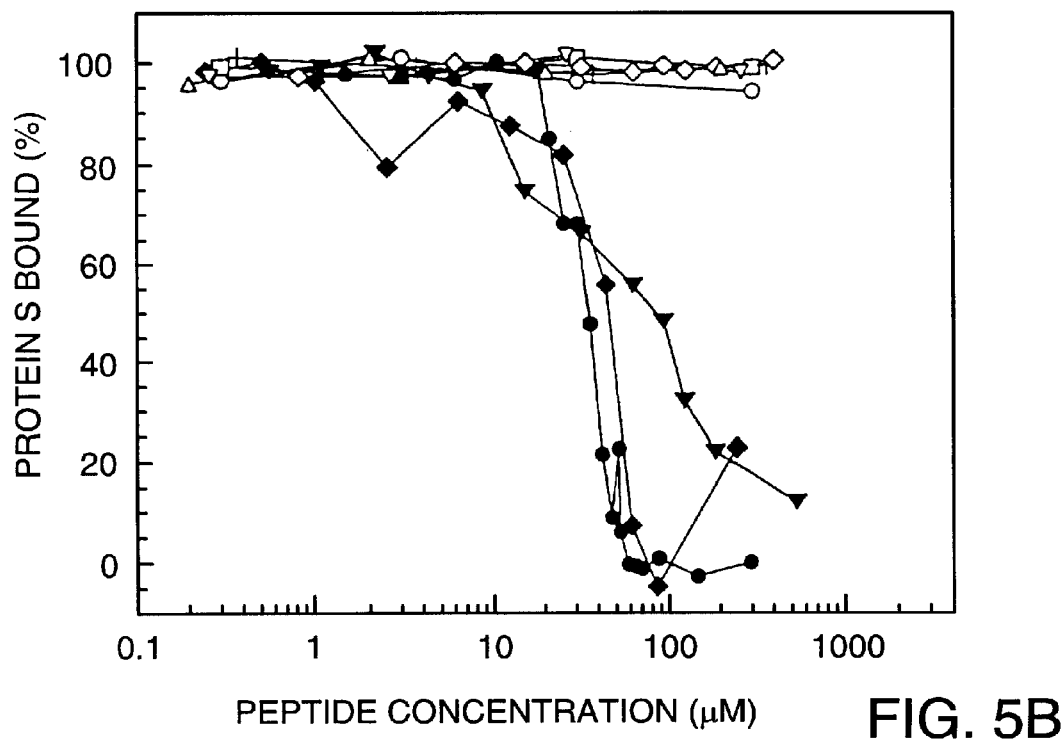

The above experimental results are shown in FIGS. 5A and 5B. In these figures, peptide inhibition of the protein S-C4BP interaction is shown as the amount of protein S bound (relative to the amount bound in the absence of peptide) versus concentration of the nine peptides listed in Table 1: (○) SL1, (♦) SL2, (□) SL3, (+) SL4, (◊) SL5, (•) SL6, (▼) SL7, (Δ) BD4 & (▽) BD6. In FIG. 5A, the result from an equilibrium binding assay using immobilized C4BP in microtiter wells and radiolabelled human protein S is shown. This panel also shows data with unlabelled protein S in competion with the radiolabelled protein S (▲). In FIG. 5B, the result from surface plasmon resonance assay on a BIAcore™ sensorchip is shown. The amount of protein S bound, X, was calculated from the observed signal intensity, S, compared to the maximum signal intensity in the absence of peptide $S_{max}$, as $X=(S-0.04)/0.96\ S_{max}$.

From the above results, it is obvious that only peptides of the present invention. i.e. peptides which comprise residues 447–460 are capable of inhibiting the protein S-C4BP interaction (SL2=439–460, SL6=447–468 and SL7=435–468). Fluorescence polar titration (results not shown) suggests that these peptides interact directly with C4BP with a dissociation constant $K_D \leq 1$ μM. The dissociation constant of the peptide-C4BP complex is thus at most 130-fold higher than the dissociation constant of the complex of $Ca^{2+}$-free protein S and C4BP ($K_D$=6,5 nM, He et al, 1996)—a reasonable result in view of the inhibition experiments in microtiter wells (performed in the absence of calcium, in EDTA containing buffer) requiring 50–100-fold more peptide than protein S to produce half maximum inhibition of the binding of the radiolabelled protein S to C4BP. The difference in $K_D$ observed for the peptide and protein might in part be due to post translational modification of the protein.

Moreover, even though the peptides of the present invention comprise an amino acid residue sequence corresponding to an amino acid sequence of mature protein S, which is close to sequences reported in prior art as likely locations of the C4BP binding site, such prior art sequences (BD4, residues 405–437, and BD6, residues 595–628), when synthesized and tested for inhibition of the protein S-C4BP interaction in the above tests, gave no inhibitory effect even when employed in 2000-fold excess over protein S.

What is claimed is:

1. A method for determining the level of free protein S in a biological fluid, said method comprising the steps of, (a) bringing a ligand, that binds specifically to free protein S, into contact with said biological fluid to form a reaction mixture comprising at least a liquid phase;

(b) maintaining said reaction mixture for a time period sufficient for said ligand to bind to free protein S in said fluid and thereby to form a protein S/ligand complex; and (c) determining the level of the complex formed in step (b) and thereby the level of free protein S in said fluid, in which method the ligand of step (a) is comprised of the extreme N-terminal SCR-module of the β-chain of the C4BP molecule.

2. The method of claim 1, wherein said ligand of step (a) is operatively linked to a solid carrier, the reaction mixture formed in step (a) being comprised of a liquid phase and a solid phase and the complex formed in step (b) being comprised in the solid phase linked to the carrier.

3. The method of claim 1, wherein the reaction mixture formed in step (a) is comprised of one phase, which is a liquid phase.

4. The method of any of claims 1, 2 or 3 wherein an indicating means is added to the mixture of step (a), said indicating means being added separately or in a form wherein it is operatively linked to or incorporated in the ligand and said indicating means being capable of producing, directly or indirectly, a detectable signal at the formation of the complex in step (b), and wherein the complex formed in step (b) comprises the indicating means and the determination in step (c) comprises measuring the amount of indicating means in said complex.

5. The method of claim 2, wherein the determination in step (c) comprises contacting the carrier-bound protein S-containing complex formed in step (b) with an antibody specific for protein S to form an immunoreaction mixture having a liquid and a solid phase and for a time period sufficient for said antibody to immunoreact with said complex to form an immunoreaction product linked to the solid phase; and determining the amount of said antibody present in said immunoreaction product, and thereby the amount of said protein S-containing complex formed in step (b).

6. The method of claim 1, wherein the ligand used in step (a) is comprised of C4BP.

7. The method of claim 1, wherein the ligand used in step (a) is comprised of at least one fragment of C4BP, said fragment comprising at least the extreme N-terminal SCR-module of the β-chain of the C4BP molecule or a hybrid molecule comprised of said C4BP fragment.

8. The method of claim 1, wherein steps (a) and (b) are performed in the presence of $Ca^{++}$ ions.

9. The method of claim 1, wherein said biological fluid is blood, plasma or serum.

* * * * *

SEQUENCE LISTING

<160> NUMBER OF SEQ ID NOS: 7

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      Peptide -continued

```
<400> SEQUENCE: 1

Leu Asp Gly Cys Ile Arg Ser Trp Asn Leu Met Lys Gln Gly Ala Ser
 1               5                  10                  15

Gly Ile Lys Glu Ile Ile Gln Glu Lys Gln Asn Lys His Cys Leu Val
             20                  25                  30

Thr

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Tyr Asn Gly Cys Met Glu Val Asn Ile Asn Gly Val Gln Leu Asp Leu
 1               5                  10                  15

Asp Glu Ala Ile Ser Lys His Asn Asp Ile Arg Ala His Ser Cys Pro
             20                  25                  30

Ser Val

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Tyr Asn Gly Cys Met Glu Val Asn Ile Asn Gly Val Gln Leu Asp Leu
 1               5                  10                  15

Asp Glu Ala Ile Ser Lys His Asn Asp Ile Arg Ala His Ser Cys Pro
             20                  25                  30

Ser Val

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Glu Lys Gly Ser Tyr Tyr Pro Gly Ser Gly Ile Ala Gln Phe His Ile
 1               5                  10                  15

Asp Tyr Asn Asn Val Ser
             20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ser Asp Gln Gln Ser His Leu Glu Phe Arg Val Asn Asn Leu Glu Lys
 1               5                  10                  15
```

```
Ser Thr Pro Leu Lys
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Asp Lys Ala Met Lys Ala Lys Val Ala Thr Tyr Leu Gly Gly Leu Pro
 1               5                  10                  15

Asp Val Pro Phe Ser Ala Thr
            20

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Leu Val Thr Val Glu Lys Gly Ser Tyr Tyr Pro Gly Ser Gly Ile Ala
 1               5                  10                  15

Gln Phe His Ile Asp Tyr Asn Asn Val Ser Ser Ala Glu Gly Trp His
            20                  25                  30

Val Asn
```